United States Patent [19]
Condon et al.

[11] Patent Number: 5,188,596
[45] Date of Patent: Feb. 23, 1993

[54] TRANSPARENT PROSTATE DILATION BALLOON AND SCOPE

[75] Inventors: Dennis E. Condon, Santa Barbara; Robert S. Bley, Goleta; Bobby K. Purkait, Santa Barbara, all of Calif.

[73] Assignee: Mentor Corporation, Santa Barbara, Calif.

[21] Appl. No.: 589,048

[22] Filed: Sep. 27, 1990

[51] Int. Cl.⁵ .......................... A61M 29/00
[52] U.S. Cl. ........................ 604/101; 604/53; 606/192; 128/6
[58] Field of Search .......... 606/108, 191–192, 606/194, 198, 7, 15; 604/53, 96–104; 128/6

[56] References Cited

U.S. PATENT DOCUMENTS

| | | | |
|---|---|---|---|
| 2,642,874 | 6/1953 | Keeling | 604/101 |
| 2,799,273 | 7/1957 | Oddo | 604/101 |
| 4,630,609 | 12/1986 | Chin | 604/101 X |
| 4,660,560 | 4/1987 | Klein | 606/108 |
| 4,738,659 | 4/1988 | Sleiman | 604/96 |
| 4,783,135 | 11/1988 | Utsumi et al. | 350/96.3 |
| 4,892,099 | 1/1990 | Ohkawa et al. | 606/194 |
| 4,932,956 | 6/1990 | Reddy et al. | 606/192 |
| 4,932,958 | 6/1990 | Reddy et al. | 606/192 |
| 4,961,738 | 10/1990 | Mackin | 606/15 |
| 5,002,558 | 3/1991 | Klein et al. | 606/192 |
| 5,007,898 | 4/1991 | Rosenbluth et al. | 604/54 |
| 5,090,959 | 2/1992 | Samson et al. | 604/96 |

Primary Examiner—C. Fred Rosenbaum
Assistant Examiner—C. Maglione
Attorney, Agent, or Firm—Blakely, Sokoloff, Taylor, Zafman

[57] ABSTRACT

The present invention comprises a prostate dilation balloon disposed on a urethral catheter, a fixation balloon also disposed on said catheter, wherein said catheter is partially or completely transparent, and a fiber optic endoscope disposed within said catheter. The scope is arranged so that it can visualize the area outside the catheter in order to determine whether the dilation balloon and fixation balloon are properly located within their respective targets within the urethra and/or bladder. The scope is also capable of focusing on objects which may be present in and along the urethra.

13 Claims, 3 Drawing Sheets

TRANSPARENT PROSTATE DILATION BALLOON AND SCOPE

BACKGROUND OF THE INVENTION

1. Field of the Invention:

This invention relates generally to the medical field of urology, and more particularly to inflatable balloons for dilation of the prostate uretha, and to methods for the treatment of benign prostatic hyperplasia using the same.

2. Art Background:

Benign prostatic hypertrophy is a common occurrence in older males. One major effect of this disorder is the constriction of the urethra within the prostate resulting in a number of symptoms in a patient, including nocturia, frequency of urination, stanguria and post-void dribbling, as well as varius related emotional and other physical problems. Currently, there are several forms of treatment for this prostate disorder, including drug therapy, hypothermia treatment, surgical treatment such as transurethral prostatectomy (TURP), implantation of prostatic stents and dilation balloon therapy.

The TURP procedure is surgical, subjecting the patient to a number of risks including post-operative bleeding, stricture formation at the urethra or bladder neck, incontinence, post-manipulation pain or bladder spasms, urinary infections, reactive urethral swelling causing urinary obstruction, epididymitis, as well as other standard problems associated with post surgery recovery. Additionally, the surgery requires 1-3 hours of operating room time, approximately a one-week recovery in the hospital and a significant amount of additional recovery time before the patient is fully able to resume normal function.

Another method for prostate treatment involves the injection or application of drugs or other medications into or adjacent the prostate gland by means of a catheter disposed adjacent the gland. This medication is frequently ineffective due to the poor absorption capability of the prostate gland as well as the difficulty in positioning and retaining the catheter with respect to the affected area. Accordingly, several patents, namely U.S. Pat. Nos. 3,977,408; 2,642,874 and 550,238, disclose the use of balloons to retain the catheter in place while medication is applied to the gland, and U.S. Pat. Nos. 2,936,760 and 550,238 also teach the use of balloons to isolate regions of the urethra in order to provide medicine to the localized area.

Dilation balloon catheters are commonly used for the removal of constrictions caused by deposits of plaque in arteries as is taught in U.S. Pat. No. 4,636,195.

There are also now several reports of the use of balloon catheters in treatment of benign prostate hypertrophy. U.S. Pat. No. 4,660,560 issued to Klein, discloses the treatment of obstructive tissue in the prostrate urethra with a balloon catheter wherein the proximal end of the catheter is anchored in the bladder by means of a Foley or fixation balloon and an annular balloon surrounding the catheter is dilated to dilate the prostate urethra. Proper location of the dilation balloon and proper sizing of the dilation balloon are critical in order to prevent having the dilation balloon being disposed in the sphincter thereby causing serious damage to the sphincter and making it impossible to control urine flow thereafter. Proper location of the annular balloon is obtained by first introducing into the urethra a cystoscope and a graduated catheter having length markings along its exterior and measuring the length of the prostate by counting the measurement lines. Once the proper size of the annular balloon is determined, it is inserted into the urethra through a disposable introducing sheath and the sheath is withdrawn to expose the dilating balloon. The position of the balloon is detected using radiological techniques. Alternatively, the position of the dilating may be detected by an endoscope inserted through the sheath adjacent the dilating balloon and its associated catheter to observe its position and ensure that the dilating catheter is entirely within the prostate. Once properly located, the positioning balloon is inflated to retain the catheter in position during the procedure. Thereafter, the dilating balloon is inflated and maintained in its inflated state for at least 10 minutes. The balloons are then deflated and the device removed. A Foley catheter may be inserted to assist in voiding for the first 1 to 2 days after the treatment. Recovery requires only several days. Preliminary studies of this treatment using the foregoing device have been favorable. (*Urology Times*, "Two-balloon Prostate Dilation Improves Voiding Symptoms" Feb. 1989, P. 1; *Surgical Practice News*, "Balloon Catheter Procedure Obviates Surgery for Benign Prostatic Hypertrophy Blockage" September 1988)

U.S. Pat. No. 4,932,956 issued to Reddy, et al. discloses a prostate balloon dilator having a fixation balloon disposed on a catheter distal to the dilation balloon. The dilation balloon need not be sized because any excess balloon merely sticks up into the bladder. The distal fixation balloon is disposed in the urethra distal to the sphincter and is localized in that position by palpation of a hardened ring disposed proximal to the fixation balloon. Localization of the balloon is also obtained by means of post-insertion radiology by detecting the radio-opaque markers disposed at critical positions along the balloon or catheter. Success with this method and apparatus in treating benign prostatic hyperplasia has been demonstrated. (Reddy, et al., *Contemporary Urology*, "Balloon dilation of the prostate: Can it help the patient with BPH?" February/March 1989, p. 44 et seq.)

As is evident from the foregoing patents, a major element of successful dilation of the prostate depends upon the proper placement of the balloon within the prostate combined with immobilization of the dilation balloon so that it does not migrate out of the prostate. It is also of utmost importance that the dilation balloon is not be expanded while it is disposed within the urethral sphincter. To ensure that the dilation balloon is not within the sphincter, the currently preferred method is to provide an cystoscope and visualize the location of the balloon to verify its location. This requires that two objects, namely the dilation catheter and the scope, be placed within the urethra. Both devices can be placed within one large sheath or catheter. However, this procedure is cumbersome and uncomfortable to the patient since such a large sheath or catheter must be placed within the urethra. It should also be noted that additional tubes for irrigation are oftentimes provided through the catheter as well. Accordingly, patients are at least anesthetized locally if not placed under general anesthesia in order to minimize the discomfort to the patient.

In our U.S. patent application Ser. No. 539,865 we disclose a ureteral stent and cystoscope combination for insertion of the stent and observation of the same. The scope in that application is in the form of a fiber optic bundle having an appropriate provision for light and lensing thereof, and preferably having a video camera and monitor responsive to the image formed at the proximal end of the scope for viewing during the scope insertion process. The fiber optic bundle itself is sufficiently small so that the entire scope may be fabricated with the appropriate dimensions and is made sufficiently flexible for movement through the urethra, the bladder and into the ureter.

SUMMARY OF THE INVENTION

The present invention comprises a prostate dilation balloon disposed on a ureteral catheter, a fixation balloon also disposed on said catheter, wherein said catheter is partially or completely transparent, and a fiber optic endoscope disposed within said catheter. The scope is arranged so that it can visualize the area outside the catheter in order to determine whether the dilation balloon and fixation balloon are properly located within their respective targets within the urethra and/or bladder. The scope is also capable of focusing on objects which may be present in and along the urethra such as growths, stones and other blockages, so that the present invention is also properly sized so that it only causes minimal discomfort to the patient during and while it is inserted into the patient's urethra. Significantly, in this regard, the scope fits within the lumen of the catheter for compact size and to provide the increased comfort over prior art devices.

In the preferred embodiment as stated above, the entire catheter is sufficiently transparent for the scope to focus on the structures outside, and particularly, to visualize the ureteral sphincter, the prostate, and when the scope is in the bladder. In an alternative embodiment, the catheter has spaced apart windows allowing the scope to view outside the catheter at preferably regular intervals, at least within the proximal 4-7 inches in order to permit visualization of the structures comprising and adjacent the prostate. The windows so provided should be localized so that they are adjacent to all critical structures, such as the sphincter, when the device is properly in position. The balloon or balloons comprising the invention are also preferably transparent to permit viewing of adjacent structures before, during and after the dilation of the dilation balloon.

In the preferred embodiment, the catheter is also provided with irrigation apparatus to provide a source of irrigation to the area as desired. The continued irrigation will also keep the field of vision relatively clear.

In an alternative embodiment, the catheter portion of the invention has graduation markers thereon so that the actual dimension can be determined by use of the scope. Alternatively a second graduated measuring device may be provided within the catheter adjacent the scope to provide size information to the user. In yet another alternative embodiment of the present invention markers visible to the scope are provided to indicate to preferred location of the prostate and sphincter, or either of them, so that the catheter is properly located in the urethra.

In various alternative embodiments of the present invention, a fixation balloon may be provided, or not used at all. If provided, the fixation balloon may be provided at the proximal end of the catheter, for fixation within the bladder, or distal to the dilation balloon for fixation distal to the prostate and sphincter.

For confirmation of proper localization, the catheter and/or fixation balloon or dilation balloon may be marked with a radiopaque material for x-ray of fluoroscopic observation, or it may be provided with a tactile detection means such as a hardened ring locatable by palpation.

The scope is in the form of a fiber optic bundle having an appropriate provision for lighting and lensing thereof, and preferably having a video camera and monitor responsive to the image formed at the opposite end of the scope for viewing during the scope insertion process. The fiber optic bundle itself is made sufficiently small so that the entire scope may be fabricated with the appropriate dimensions so that it may fit within a typical catheter and made sufficiently flexible for negotiating a tortuous path as required.

DETAILED DESCRIPTION OF THE INVENTION

Figure 1:
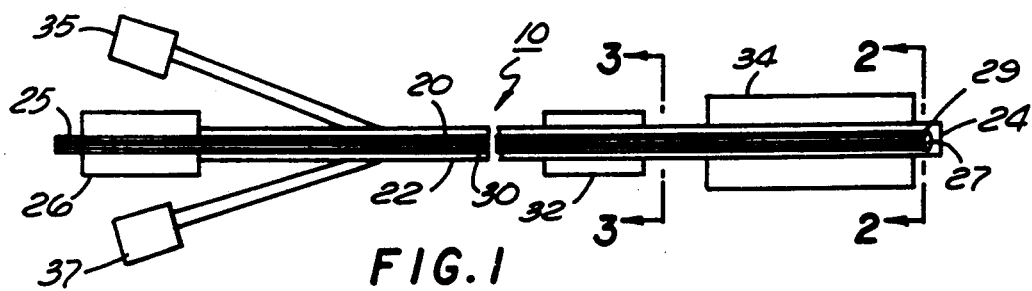
FIG. 1 is an illustration, not to scale, of a cross-section of the subject invention from a side view thereof.
Figure 2:
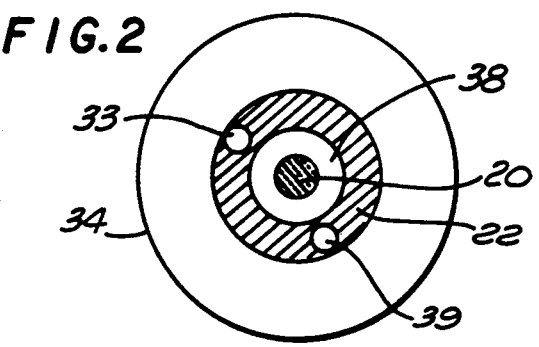
FIG. 2 is an enlarged sectional view of the subject invention taken through lines 2—2 of FIG. 1, also not to scale.
Figure 3:
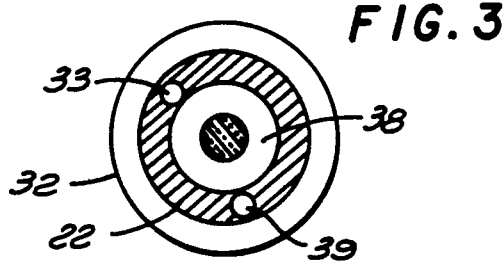
FIG. 3 is an enlarged sectional view of the subject invention taken through lines 3—3 of FIG. 1, also not to scale.

First, referring to FIG. 1, a schematic diagram (not to scale) of a typical system in accordance with one embodiment of the present invention may be seen. As shown therein, a long, small-diameter fiber optic scope generally indicated by the numeral 20 extends through the catheter 22 of the present invention 10. For reference, the catheter 22 has a proximal end 24 and a distal end 26, the proximal end being the end inserted into the patient's body and the distal end 26 being the end remaining outside the patient's body in use. As shown in FIGS. 1 and 2, disposed within catheter 22 is its interior 38 which contains a fiber optic bundle 20 having a lens 27 on its proximal end 29 to provide a focused image on the fiber optic bundle 20. As discussed in more detail in our co-pending patent application Ser. No. 539,865, the scope 20 has a light source which feeds a fraction of the optical fibers 30 with sufficient light to adequately illuminate the region surrounding the proximal end 29 of the scope so that an image of adequate intensity and contrast may be received at the proximal end 29 of the fiber optic image bundle. Also at the distal end 25 of the scope 20, adjacent to the light source is a video camera (not shown) with appropriate lenses to convert the image at the distal end to a video signal to display on a video monitor. The catheter 22 has disposed on it two annular balloons, in the preferred embodiment, a first annular balloon comprising a fixation balloon 32 and a second annular balloon comprising a dilation balloon 34 for dilating the prostatic urethra as is known in the art. The dilation balloon 34 and fixation balloon 32 are filled through ports 35 and 37, respectively. The ports 35 and 37 attach to conduit 33 and 39 respectively which is in direct communication with the respective balloons. The conduit may be individual tubes disposed in said catheter, may be fixed sections of said catheter, may be disposed within the walls of said catheter, or may be disposed outside said catheter, as will be appreciated by a person of ordinary skill in the art. As shown in FIGS. 2 and 3, which are enlarged, sectional views of the subject invention shown in FIG. 1, the scope 20 made up of the fibers 30 is disposed within the catheter 22 which is surrounded by annular dilating balloon 34 as shown in FIG. 2 and annular fixation balloon 32 as shown in FIG. 3. Conduit 33 and 39 are shown there disposed within the walls of said catheter.

In the preferred embodiment, the catheter 22 is made of a transparent material so that the scope 20 can view outside thereof to observe the location of the dilation balloon and fixation balloon relative to the various structures of the urological system. Most importantly, it is important to note that the dilation balloon 34 is disposed within the prostate and that none of the dilation balloon is disposed in the sphincter, for the reason that dilating the dilation balloon while it is disposed in the sphincter could cause permanent damage to the sphincter resulting an inability to stop urinating. Similarly, it is important to note that the fixation balloon 32 is, if the device is configured as shown in FIG. 1 for example, disposed distal to the sphincter. Similarly, if the device is configured as shown, for example in FIG. 6, the fixation balloon should be localized in the bladder and observed therein utilizing the scope of the present invention. In the embodiment shown in FIG. 1, the entire catheter is transparent. Additionally, and preferably, the balloons 32 and 34 should also be transparent. Various materials could be used in the manufacture of the catheter 20 and balloons 32 and 34 in order to make them transparent. For example, they could be made out of polyvinyl chloride (PVC) or polyethylene terephthalate (PET).

Figure 4:
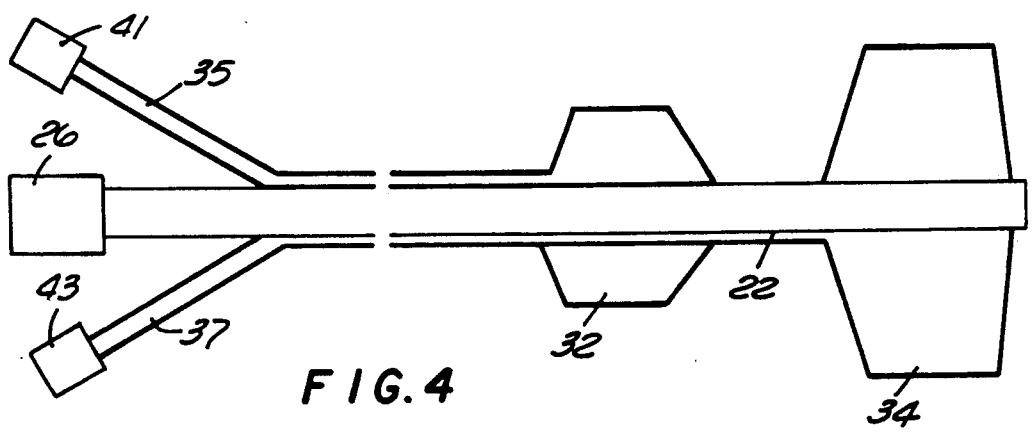
FIG. 4 is an enlarged schematic view of the subject invention, not to scale, showing the interconnection of the dilation and fixation balloons to the fill ports for each of them.

Now referring to FIG. 4, a schematic of the subject invention not to scale is shown to illustrate the dilation of the various balloons. In FIG. 4 the scope is removed for easier visualization of the invention. Filling port 35 is in fluid communication with fixation balloon 32 so that when fluid is inserted under pressure through filling port 35 balloon 32 expands. Similarly, filling port 37 is in fluid communication with dilation balloon 34 so that insertion of fluid through port 37 dilates balloon 34.

Figure 5:
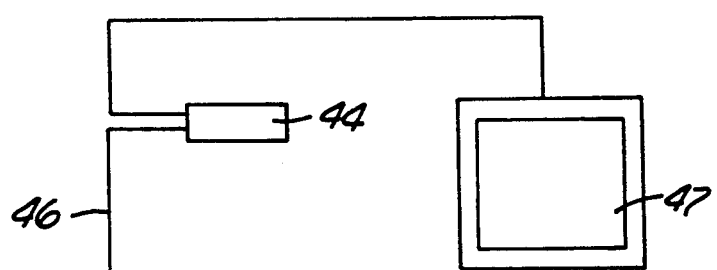
FIG. 5 is a schematic view of the subject invention interconnected to a television viewing system.
Figure 5:
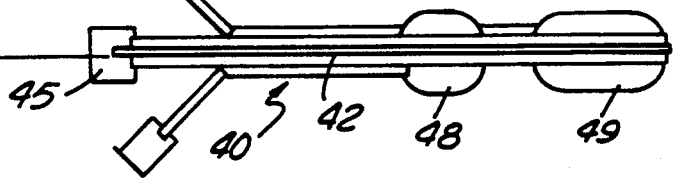

FIG. 5 illustrates the entire system of the subject invention. As shown in FIG. 5, the balloon catheter system 40 having scope 42 disposed therein. The scope 42 obtains an image which is transmitted through its fiber optic bundle to camera 45 converting the image into an electrical signal which is transferred via electrical connectors 46 to processor 44 which in turn transmits the image to remote television 47. In this way, the physician performing the procedure can view the interior of the urethra as well as the placement of the balloons 48 and 49 within the urethra.

Figure 6:
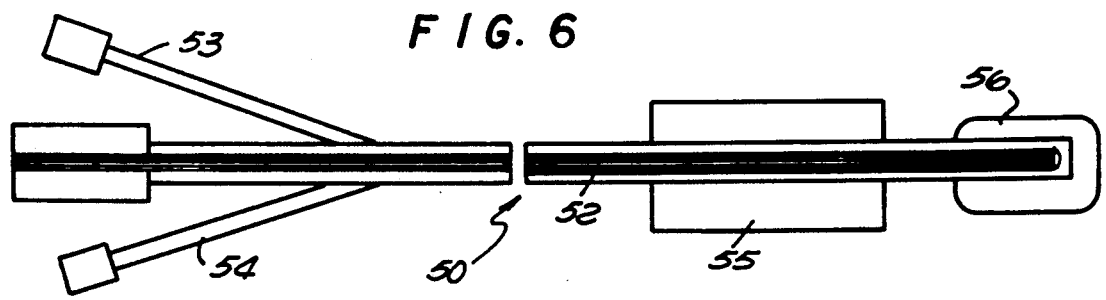
FIG. 6 is an illustration, not to scale, of a cross-section of an alternative embodiment of the subject invention in which the dilation balloon is disposed distal to the fixation balloon, from a side view thereof.

FIG. 6 shows an alternative embodiment of the present invention in which the endoscope 52 is disposed in a catheter 50 having a fixation balloon 56 disposed on the proximal end thereof and the dilation balloon 55 being disposed distal to said fixation balloon. Filling ports 53 and 54 are provided to fill the dilation and fixation balloons. Preferably, but not necessarily, the balloons are also transparent to permit view therethrough of structures in and around the urethra, prostate and bladder. Prostatic balloon catheter of this type, as described in the background section above, are used by retaining the fixation balloon within the bladder of a patient in use.

Figure 7:
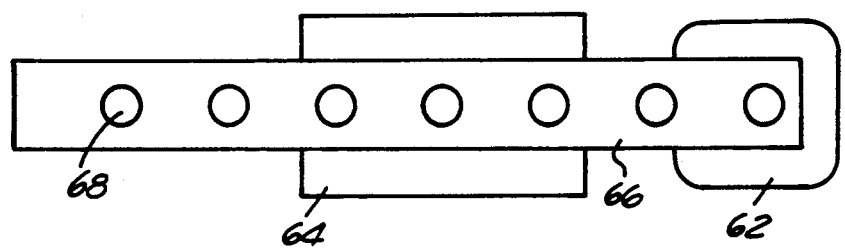
FIG. 7 is an enlarged side view of the catheter and balloon portion of the subject invention, without the scope, in yet another alternative embodiment wherein windows are disposed through the wall of an otherwise non-transparent catheter.

FIG. 7 is yet another alternative embodiment of the present invention. FIG. 7 shows a portion of the urethral catheter and balloons without the scope. The catheter 66 is not transparent as it is in the prior embodiments, but instead, is comprised of a non-transparent wall with a plurality of holes or windows 68 disposed in the walls of the catheter to enable the scope when disposed therein to view outward through the holes to the exterior of the catheter 66. The holes are preferably, but not necessarily, regularly spaced apart at determinable intervals so that measurements can be taken, if necessary, by counting the number of holes disposed along the portion of the body to be measured. It will be appreciated by a person of ordinary skill in the art that while the balloons 62 and 64 are set forth in the shown relationship, the alternative relationship as shown in FIG. 1 wherein the dilating balloon is disposed proximally to the fixation balloon is also possible.

Figure 13:
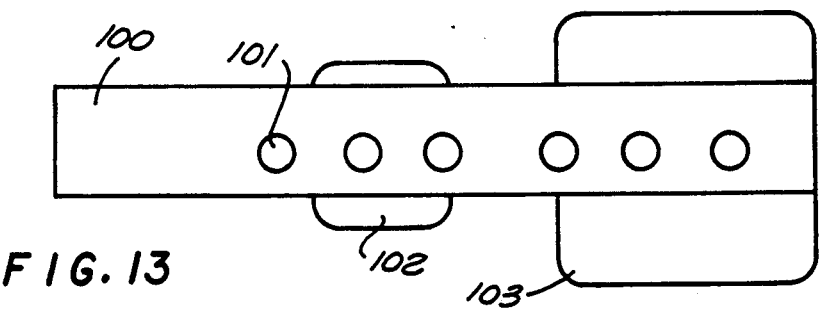
FIG. 13 is an enlarged side view of the catheter and balloon portion of the subject invention, without the scope, in yet another alternative embodiment wherein windows are disposed in a predetermined arrangement through the wall of an otherwise non-transparent catheter.

As shown in FIG. 13, the windows 101 disposed within catheter 100 need not be regularly spaced along the catheter 100, but can be disposed in predetermined positions along the catheter and adjacent or near the fixation balloon 102 and dilation balloon 103.

Figure 8:
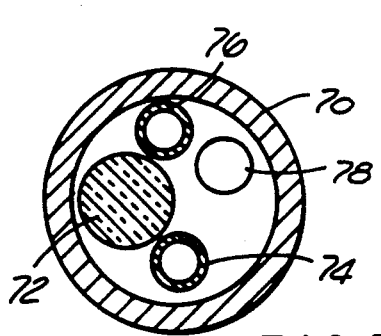
FIG. 8 is a cross-sectional view of another embodiment of the subject invention taken through the catheter.

FIG. 8 shows a sectional view of an alternative embodiment of the present invention. The balloons are not shown in FIG. 8. The catheter 70 has disposed therein a fiber optic bundle 72 for carrying the image focused on the end thereof to the television camera. Conduits 74 and 76 carry fluid from the dilation ports to the respective balloons. Conduit 78 may be used to dispense fluid for continuous or intended intermittent irrigation of the surgical area and the like.

Figure 9:
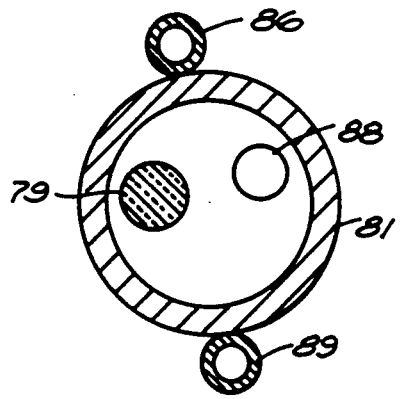
FIG. 9 is a cross-sectional view of another embodiment of the subject invention taken through the catheter showing an alternative arrangement of the balloon filling conduit.

FIG. 9 shows a sectional view of an alternative embodiment of the present invention with the conduit for filling the balloons in an alternative arrangement. The balloons are not shown in FIG. 9. The catheter 81 has disposed therein a fiber optic bundle 79 for carrying the image focused on the end thereof to the television camera. Conduits 89 and 86 are disposed outside the wall of the catheter 81 to carry fluid from the dilation ports to the respective balloons. Conduit 88 may be used to dispense fluid for continuous or intended intermittent washing of the surgical area and the like.

Figure 10:
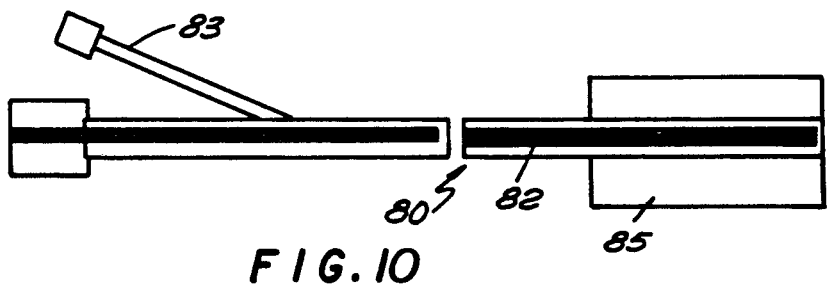
FIG. 10 is an illustration, not to scale, of a cross-section of an alternative embodiment of the subject invention in having only a dilation balloon.

It will be appreciated by a person of ordinary skill in the art that while fixation balloons are provided for ease of use, they are not essential to dilation process and may be elimated without departing from the spirit and scope of the present invention. Accordingly, FIG. 10 illustrates such an embodiment wherein the catheter 80 has only a single filling port 83 to fill dilation balloon 85.

Figure 11:
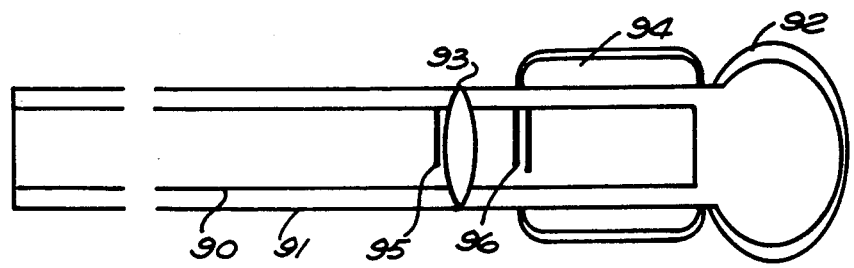
FIG. 11 is an enlarged schematic side view of another embodiment of the present invention disposed within the urethra of a patient illustrating markers for indicating the proper positioning of the catheter.

FIG. 11 illustrates an alternative embodiment of the present invention in which markers are provided to indicate the proper positioning of the catheter. FIG. 11 is a cross-sectional schematic view of the invention inserted in the urethra, with the scope and balloons deleted for clarity. The catheter 90 is disposed within the urethra 91 up to the bladder 92, although it will be appreciated by a person of ordinary skill in the art that the catheter could extend into the bladder for certain embodiments of the invention. A schematic view of the sphincter 93 and prostate 94 are also shown for illustrative purposes. In this embodiment, the catheter 90 has markings which are visible to the scope to indicate where the catheter should be position relative to the sphincter 93 and/or prostate 94. The sphincter marking 95 is shown as a single line, and indicates approximately where the sphincter should align relative to the catheter. The prostate marking 96 is shown as a double line indicating where the distal end of the prostate should be aligned. It will be appreciated by a person of ordinary that many different types of markings can be utilized without departing from the spirit and scope of the present invention. The markings may be provided on the inside or outside wall of the catheter, or on a separate structure within the catheter. The markings may be inked or painted on, or may be raised, scratched, embossed or the like in the catheter.

Figure 12:
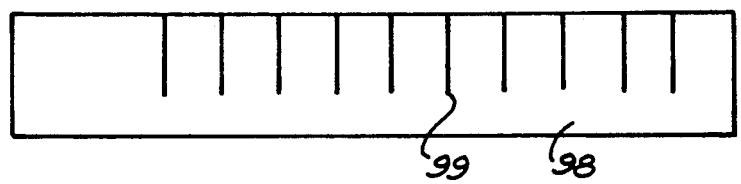
FIG. 12 is an enlarged side view of another embodiment of the present invention illustrating the markers for indicating the proper alignment of the catheter adjacent the sphincter and prostate.

As shown in FIG. 12, the catheter 98 can otherwise (or additionally) have regularly spaced markings 99 so that measurements may be taken to determine the distances between various structures along a patient's urological system, including the distance between the sphincter and prostate and bladder, and the length of the prostate.

Figure 14:
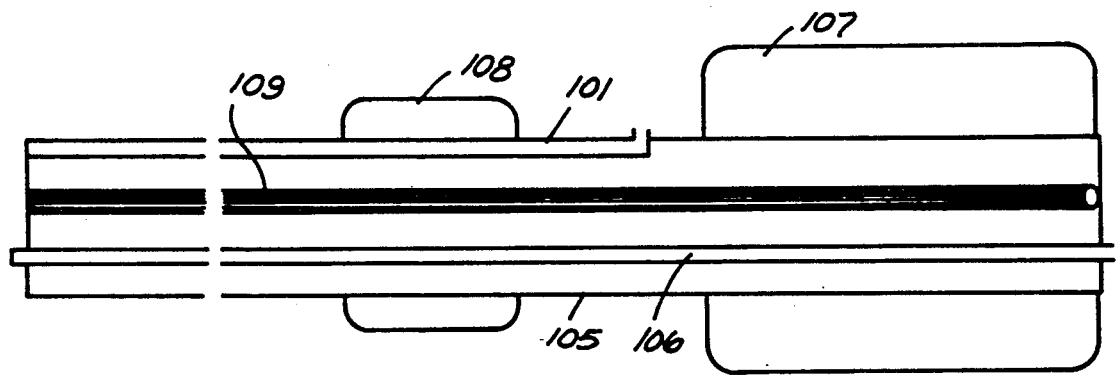
FIG. 14 is an enlarged side view of the the present invention, not to scale, illustrating an irrigation system.

FIG. 14 depicts another embodiment of the present invention in which one or more irrigation means are provided for irrigating the bladder and also the volume between the two balloons. Of course, an irrigation system having either of the irrigation means of FIG. 14 may be employed within the scope of the present invention. As shown in FIG. 14, the catheter 105 has a first irrigation conduit 106 which irrigates the volume proximal to the dilation balloon 107; that is, into the bladder. The second irrigation conduit 110 irrigates the volume between the dilation balloon 107 and the fixation balloon 108. The scope 109 is also shown.

In using the subject invention, the catheter with the balloons is first inserted through the urethra and the balloons are generally placed in the proper area. The placement of the balloons in the desired target areas may be monitored by the use of the scope which is disposed usually near the end of the catheter, but is movable within the catheter so that movement and localization can be observed along the entire length of the catheter. When the catheter and the balloons are generally in place, the scope is utilized to ensure that the fixation balloon is properly in place prior to inflation of the same. Additionally, as the fixation balloon is inflated, the urethra adjacent around the fixation balloon can be continuously monitored to make sure that the balloon does not migrate to a position that is debilitating to the patient, such as within the sphincter, and to observe any other physiological phenomenon that may occur along the urethra. After the fixation balloon is fully inflated, the dilation balloon may be inflated in accordance with the procedures of the prior art. After the treatment is completed, the balloons are deflated and it may be observed through the scope whether the balloons are completely deflated in order to provide maximum protection for the patient while the catheter is being removed from the patient.

It will be appreciated by a person of ordinary skill in the art that while the present invention has been disclosed and described herein with respect to certain preferred embodiments and alternatives thereof, various changes in form and detail may be made therein without departing from the spirit and scope thereof.

What is claimed is:

1. A system for dilation of the prostate urethra comprising:
    a urinary catheter for insertion in the prostate urethra, said catheter having proximal and distal sections, said catheter being partially transparent;
    a flexible, resilient, transparent dilation balloon mounted on said catheter;
    a first filling means operatively connected to said dilation balloon for inflating said dilation balloon;
    a flexible, resilient, transparent fixation balloon mounted on said catheter;
    a second filing means operatively connected to said balloon for inflating said fixation balloon;
    an elongate flexible scope means extending through said catheter for viewing at said proximal section of said catheter, said scope means having a first scope end at said proximal section of said catheter and a second scope end at said distal section of said catheter, said scope means including:
        illumination means for illuminating objects in the vicinity of said first scope end;
        imaging means adjacent said first end thereof for providing an image of objects in the vicinity of said first end of said scope means; and
        conveying means for conveying the image provided by said imaging means to the second end of said scope for viewing when said scope is inserted into said catheter, whereby said scope means may provide a viewing capability through the transparent portion of the catheter.

2. The dilation system of claim 1 wherein said catheter is completely transparent.

3. The dilation system of claim 1 further comprising conduit means for providing fluid to said proximal section for rinsing the area adjacent thereto.

4. The dilation system of claim 1 wherein said catheter comprises a plurality of spaced apart windows disposed therein to permit the viewing by said scope of the area outside said catheter.

5. The dilation system of claim 4 wherein said windows are disposed in predetermined positions adjacent said balloons to ensure visualization of said balloons relative to physiological structures in and adjacent the urethra of a patient in use.

6. The dilation system of claim 1 wherein said catheter further comprises at least one marker disposed on said catheter indicating the proper position of said catheter relative to a patient's prostate in use.

7. The dilation system of claim 6 wherein said catheter further comprises a marker indicating the proper position of said catheter relative to a patient's sphincter in use.

8. The dilation system of claims 6 or 7 wherein said marker is disposed within said catheter.

9. The dilation system of claim 1 further comprising an irrigation means extending through said catheter for irrigating the urethra and adjacent physiological structures of a patient in use.

10. The dilation system of claim 9 wherein said irrigation means provides irrigation proximally and distally from the dilation balloon.

11. The dilation system of claim 1 wherein said transparent catheter is made of materials selected from polyvinyl chloride and polyethylene terephthalate.

12. A method of performing dilation therapy to a prostate comprising the steps of:
   providing a system for dilation of the prostate urethra comprising:
      a urinary catheter for insertion in the prostate urethra, said catheter having proximal and distal sections;
      a flexible, resilient dilation balloon mounted on said catheter;
      a first filling means operatively connected to said dilation balloon for inflating said dilation balloon;
      a flexible, resilient fixation balloon mounted on said catheter;
      a second filling means operatively connected to said fixation balloon for inflating said fixation balloon;
      an elongate flexible scope means extending through said catheter for viewing said proximal end of said catheter, said scope means having a first scope end at said proximal section of said catheter and a second scope end at said distal section of said catheter, said scope means including;
   illumination means for illuminating objects in the vicinity of said first scope end;
   imaging means adjacent said first end thereof for providing an image of objects in the vicinity of said first end of said scope means;
   conveying means for conveying the image provided by said imaging means to the second end of said scope for viewing when said scope is inserted into a patient's urinary tract;
   inserting said catheter into the urethra of the patient;
   inserting the scope into said catheter;
   determining the position of said balloons relative to the prostate and sphincter of the patient by viewing the prostate and sphincter through said scope to ensure that said balloons are properly localized prior to inflation thereof;
   inflating said balloons for a predetermined period of time to effect treatment of said prostate;
   deflating said balloons; and
   removing said catheter from said urethra of said patient.

13. The method of claim 12 wherein said catheter has a marker and the prostate of said patient is aligned with said marker disposed on said catheter.

* * * * *